US009345681B2

(12) United States Patent
Ishida et al.

(10) Patent No.: US 9,345,681 B2
(45) Date of Patent: May 24, 2016

(54) ANTI-OBESITY AGENT COMPRISING HIGH-PURITY EPA

(75) Inventors: Takayuki Ishida, Shizuoka (JP); Hiroyuki Kawano, Shizuoka (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/129,890

(22) PCT Filed: Jul. 6, 2012

(86) PCT No.: PCT/JP2012/067337
§ 371 (c)(1),
(2), (4) Date: Feb. 7, 2014

(87) PCT Pub. No.: WO2013/005834
PCT Pub. Date: Jan. 10, 2013

(65) Prior Publication Data
US 2014/0155442 A1    Jun. 5, 2014

(30) Foreign Application Priority Data

Jul. 7, 2011    (JP) ................. 2011-151113

(51) Int. Cl.
| | | |
|---|---|---|
| A61K 31/20 | (2006.01) |
| A61K 31/21 | (2006.01) |
| A61K 31/22 | (2006.01) |
| A61K 31/42 | (2006.01) |
| A61K 31/232 | (2006.01) |
| A61K 45/06 | (2006.01) |
| A61K 31/202 | (2006.01) |
| A61K 31/167 | (2006.01) |
| A61K 31/421 | (2006.01) |

(52) U.S. Cl.
CPC ............ *A61K 31/232* (2013.01); *A61K 31/167* (2013.01); *A61K 31/202* (2013.01); *A61K 31/421* (2013.01); *A61K 45/06* (2013.01)

(58) Field of Classification Search
CPC ............ A61K 2300/00; A61K 31/167; A61K 31/202; A61K 31/232; A61K 31/421; A61K 45/06
USPC .................................. 514/376, 513, 549, 560
See application file for complete search history.

(56) References Cited

U.S. PATENT DOCUMENTS

| | | |
|---|---|---|
| 7,652,049 B2 | 1/2010 | Ali et al. |
| 2007/0112071 A1 | 5/2007 | Bryhn et al. |

FOREIGN PATENT DOCUMENTS

| | | | |
|---|---|---|---|
| JP | 2007-514733 A | 6/2007 | |
| JP | 2008-505120 A | 2/2008 | |
| WO | WO 2005/060954 A1 | 7/2005 | |
| WO | WO 2008115529 A1 * | 9/2008 | ............. A61K 31/40 |

OTHER PUBLICATIONS

Ikemoto et al., "High-Fat Diet-Induced Hyperglycemia and Obesity in Mice: Differential Effects of Dietary Oils", 1996, Metabolism, vol. 45, Issue 12, pp. 1539-1546.*
Kajikawa et al., "Highly purified eicosapentaenoic acid prevents the progression of hepatic steatosis by repressing monounsaturated fatty acid synthesis in high-fat/high-sucrose diet-fed mice", Apr. 2009, Prostaglandins, Leukotrienes and Essential Fatty Acids, vol. 80, Issue 4, pp. 229-238.*
English translation of the International Preliminary Report on Patentability and Written Opinion mailed Jan. 16, 2014, in PCT International Application No. PCT/JP2012/067337.
Li et al., "Anti-obesity effects of conjugated linoleic acid, docosahexaenoic acid, and eicosapentaenoic acid," Mol. Nutr. Food Res. (2008), vol. 52, pp. 631-645.
Perez-Matute et al., "Eicosapentaenoic acid actions on adiposity and insulin resistance in control and high-fat-fed rats: role of apoptosis, adiponectin and tumour necrosis factor-α," British Journal of Nutrition (2007), vol. 97, pp. 389-398.
Sato et al. "Antiobesity Effect of Eicosapentaenoic Acid in High-Fat/High-Sucrose Diet-Induced Obesity," Diabetes (2010), vol. 59, pp. 2495-2504.
Spady et al., "Dietary saturated triacylglycerois suppress hepatic low density lipoprotein receptor activity in the hamster," Proc. Natl. Acad. Sci. USA (Jul. 1985) vol. 82, pp. 4526-4530.
Spady et al., "Kinetic Constants for Receptor-dependent and Receptor-independent Low Density Lipoprotein Transport in the Tissues of the Rat and Hamster," J. Clin. Invest. (May 1986), vol. 77, pp. 1474-1481.
Spady et al., "Rates of receptor-dependent and -independent low density lipoprotein uptake in the hamster," Proc. Natl. Acad. Sci USA (Jun. 1983), vol. 80, pp. 3499-3503.
Tsutsumi et al., "The Relationship Between Plasma High Density Lipoprotein Cholesterol Levels and Cholesteryl Ester Transfer Protein Activity in Six Species of Healthy Experimental Animals." Biol. Pharm. Bull., (2001), vol. 24, No. 5, pp. 579-581.
Extended European Search Report for European Application No. 12807030.7, dated Jan. 21, 2015.
Nozaki et al., "Effects of Purified Eicosapentaenoic Acid Ethyl Ester on Plasma Lipoproteins in Primary Hypercholesterolemia," International Journal of Vitamin and Nutrition Research, vol. 62, No. 3, Jan. 1992, pp. 256-260, XP009132430.
Satoh et al., "Purified Eicosapentaenoic Acid Reduces Small Dense LDL, Remnant Lipoprotein Particles, and C-Reactive Protein in Metabolic Syndrome," Diabetes Care, vol. 30, No. 1, Jan. 2007, pp. 144-146, XP-002677407.

* cited by examiner

*Primary Examiner* — My-Chau T Tran
(74) *Attorney, Agent, or Firm* — Birch, Stewart, Kolasch & Birch, LLP

(57) ABSTRACT

The present invention provides an agent for preventing the increase in a body weight (or for decreasing a body weight) or an anti-obesity agent each comprising at least one component selected from the group consisting of EPA and pharmaceutically acceptable salts, esters and derivatives thereof as an active ingredient for obesity in which the increase in the formation of hepatic lipid or the occurrence of fatty liver is mild, preferably the increase in the formation of hepatic lipid or the occurrence of fatty liver is not observed.

21 Claims, 2 Drawing Sheets

ANTI-OBESITY AGENT COMPRISING HIGH-PURITY EPA

TECHNICAL FIELD

This invention relates to an agent for suppressing body weight gain (for reducing body weight) in obesity and an anti-obesity agent for the obesity wherein the agent comprises icosapentaenoic acid.

BACKGROUND ART

Intake of high fat diet is steadily increasing with the recent westernization of the Japanese life style. According to the report of the National Health and Nutrition Survey of 2008, proportion of the energy taken from the lipid in the entire energy intake is 24.9% on the average and people with high triglyceride level (greater than 110 mg/dl) or high cholesterol value (greater than 200 mg/dl) have reached about 50 to 60% at the age of 40 or higher (see Non-Patent Literature 1).

Obesity caused by the condition such as excessive fat intake has become a great social concern due to the increase in the number of patients and health risk. The obesity is the condition of excessive accumulation of adipose tissue. The standard is different by the country, and, in the diagnostic criteria of Japan Society for the Study of Obesity, obesity is defined as a body-mass index (hereinafter abbreviated as "BMI") in excess of 25, and of such obesity, the pathological condition actually or estimated to be with the health problem caused by or associated with the obesity (at least one of 10 items including type 2 diabetes, dyslipidemia, and hypertension) and medically requiring weight decrease; and visceral fat type obesity confirmed by an umbilical CT scan with the BMI of at least 25 and doubt of upper body obesity, are defined as obesity syndrome (see Non-Patent Literature 2).

The body weight gain (obesity) caused by such cause is a risk factor for the onset of metabolic syndrome observed as dyslipidemia (which is hypercholesterolemia or hypertriglyceridemia (hereinafter also abbreviated as "hyper TG"), this also applies to the following description), hypertension, arteriosclerosis, diabetes, and obesity, and prevention of the body weight gain (obesity) is important for the prevention of the metabolic syndrome. The metabolic syndrome induces vascular complication such as peripheral vascular insufficiency, ischemic heart disease, and cerebral infarction, and the quality of life will be markedly impaired for the rest of life (see Non-Patent Literature 3).

Obesity is divided into two types, namely, essential obesity (simple obesity) and symptomatic obesity (concomitant obesity) depending on the cause. The essential obesity is the obesity caused by the accumulation of the excessive energy in the form of fat and this takes place when energy intake is in excess of the consumed energy. At least 90% of the obesity is said to be this type. Examples of the cause of such obesity include lack of exercise, wrong feeding pattern, stress, dyslipidemia (lipid metabolism disorder), excessive secretion of insulin, increase of adipocyte, and insufficiency of brown adipocyte. On the other hand, onset of the symptomatic obesity is induced by other diseases such as endocrinological obesity, hereditary obesity, hypothalamic obesity, and pharmacological obesity (see Non-Patent Literature 4).

The essential obesity is divided into two types by the location of the fat, and these two types are obesity due to subcutaneous fat (peripheral obesity) and abdominal visceral fat obesity (central obesity). The subcutaneous fat is the fat immediately below the skin, and the subcutaneous fat is often associated with an increased number of adipocytes. On the other hand, the abdominal visceral fat is the fat accumulated in the mesenterium in the peritoneal cavity, and the fat is likely to be accumulated in each adipocyte. Increased abdominal visceral fat is likely to induce metabolic abnormality, and diseases such as diabetes, hypertension, arteriosclerosis, hyperlipidemia, and fatty liver are said to be easily induced under such condition.

Fatty liver is the condition of excess accumulation of fat (and mainly neutral fat or triglyceride) in the liver, and in particular, in the hepatocyte. In medicine, fatty liver means the condition wherein lipid vacuole is found in at least 30% of the hepatocyte; the condition wherein the hepatocyte contains at least 10% by weight of the fat; or the condition wherein lipid droplet in the hepatocyte is found in at least 1/3 of the hepatocytes. The fatty liver also means the condition involving the enhancement of hepatic lipogenesis in the liver, which is the cause of the onset of the fatty liver. (See Non-Patent Literatures 5 and 6).

Typical causes of the fatty liver are overnutrition, obesity, excessive alcohol intake, and diabetes, while the fatty liver is also caused by other endocrine disorders and metabolic diseases, intake of particular drugs, and on rare occasion, by excessive undernutrition. More specifically, typical causes of the fatty liver include: (1) excessive intake of dietary fat and sugar, (2) enhanced lipogenesis in the liver, (3) enhanced triglyceride formation in the liver, (4) dysfunction of the decomposition of fatty acid and triglyceride in the liver, (5) increase in the amount of free fatty acid flowing into the liver, and (6) defect of lipoprotein secretion from the liver into the blood (see Non-Patent Literatures 5 and 6).

The body weight gain (obesity) can be efficiently prevented by consumption of the ingested calories through exercise and/or decrease of calory intake by dietary restriction. The dietary restriction can be accomplished only by strict nutrition education and control, and reliable dietary restriction in normal life would be associated with considerable difficulty. Drug therapy, which may be another choice, is associated with the problems of side effects. Accordingly, if accumulation of the dietary fat in the body can be suppressed in a safe and healthy way, such method would be a practical and useful choice in treating the obesity and related diseases (for example, dyslipidemia, hypertension, arteriosclerosis, and diabetes) and promoting the health.

Despite many reports on influence of the $\omega3$ fatty acid on the obesity (see, for example, Non-Patent Literature 7), there is obviously plenty of scope for investigation. Bryhn et al. reports an experiment conducted by administering a $\omega3$ fatty acid composition (a mixture of icosapentaenoic acid (hereinafter abbreviated as "EPA") and docosahexaenoic acid (hereinafter abbreviated as "DHA")) to the mouse which had been fed on a high fat diet to thereby suppress the body weight gain. However, they failed to properly identify the effective component, and argued that DHA was the substance that contributed for the activity of suppressing the body weight gain (see Patent Literature 1).

Sato et al. reports that high purity ethyl icosapentate (hereinafter abbreviated as "EPA-E") was effective in suppressing the body weight gain in a model mouse which had been continuously fed on a high-fat and high-sugar diet suffering from obesity associated with enhanced hepatic lipogenesis or fatty liver while it was ineffective in a model mouse which had been continuously fed on a high-fat diet suffering from obesity not associated with the enhancement of hepatic lipogenesis or fatty liver (see Non-Patent Literature 8).

Hamster is an animal which has been reported to be quite suitable in studying the regulation and mechanism of the influence of the diet on the lipid-related parameters (body weight and plasma lipid markers). The observation in hamsters has also been reported to correspond to the phenomena in human (See Non-Patent Literature 9, 10, or 11).

There is a report that, in human plasma, high-density lipoprotein cholesterol value (hereinafter abbreviated as "HDL-C value") is regulated by the cholesteryl ester transfer protein (hereinafter abbreviated as "CETP"). CETP activity is little found in mouse, rat, and dog while its presence has been confirmed in hamster, rabbit, and monkey, and investigation on the CETP activity has been conducted based on such finding (see Non-Patent Literature 12).

CITATION LIST

Patent Literature

[Patent Literature 1] JP 2007-514733 A

Non-Patent Literature

[Non-Patent Literature 1] National Health and Nutrition Survey of 2008, Part 3, Results of Physical Condition Survey (in Japanese), pp. 183-236 (Ministry of Health, Labor and Welfare, January, 2011).
[Non-Patent Literature 2] "Obesity Research (in Japanese)", 2000, vol. 6, No. 1, p. 18.
[Non-Patent Literature 3] Nanzan-do Dictionary of Medicine (in Japanese), 19th edition, Nanzan-do, March, 2006: 2265.
[Non-Patent Literature 4] Journal of Japanese Society of Internal Medicine (in Japanese), 2006, vol. 96, p. 917.
[Non-Patent Literature 5] The Digestive Organ Now (in Japanese), No. 44, pp. 4-5 (Foundation of The Japanese Society of Gastroenterology, Mar. 20, 2009).
[Non-Patent Literature 6] Clinical Gastroenterology (in Japanese), 2000, vol. 15, pp. 147-155.
[Non-Patent Literature 7] Molecular Nutrition & Food Research, vol. 52, pp. 631-645, 2008.
[Non-Patent Literature 8] "Diabetes", vol. 59, pp. 2495-2504, 2010.
[Non-Patent Literature 9] Proceedings of the National Academy of Sciences of the United States of America, vol. 80, pp. 3499-3503, 1983.
[Non-Patent Literature 10] Proceedings of the National Academy of Sciences of the United States of America, vol. 82, pp. 4526-4530, 1985.
[Non-Patent Literature 11] The Journal of Clinical Investigation, vol. 77, pp. 1474-1481, 1986.
[Non-Patent Literature 12] Biological & Pharmaceutical Bulletin, vol. 24, No. 5, pp. 579-581, 2001.

SUMMARY OF INVENTION

Technical Problem

An object of the present invention is to provide an EPA-comprising agent for suppressing body weight gain (for reducing body weight) or an EPA-comprising anti-obesity agent for the obesity, in particular, the obesity of the type wherein enhancement of hepatic lipogenesis or fatty liver is mild or preferably not recognized.

Solution to Problems

The inventors of the present invention made an intensive investigation to obviate the problems as described above, and focused on the fact that hamster having CETP which is considered to be a model animal more similar to human is more suitable than mouse and rat lacking CETP normally used in the art. The inventors then found that the EPA-E exhibits very strong activity of suppressing the body weight gain and reducing the body weight as well as the activity of suppressing the increase of the CETP activity and low-density lipoprotein cholesterol (hereinafter abbreviated as "LDL-C") in the obesity model hamster fed on a high fat diet. The inventors also found that ethyl docosahexaenoate (hereinafter abbreviated as "DHA-E") which is an unsaturated fatty acid of the same group does not exhibit suppressive effect for the body weight gain, but rather have the effect of increasing the LDL-C level and the CETP activity, and that correlation is found between the LDL-C level and the CETP activity value. The present invention has been completed on the bases of such findings. Various embodiments of the present invention are described in the following.

(1) An agent for suppressing body weight gain (for reducing body weight) or an anti-obesity agent for obesity, and in particular, obesity of a type wherein enhancement of hepatic lipogenesis or fatty liver is mild and preferably not recognized, wherein the agent comprises at least one member selected from EPA and pharmaceutically acceptable salts, esters, and derivatives thereof as its effective component.

The obesity intended in the present invention is at least one obesity selected from the group consisting of obesities exhibiting EMI of at least 25, and wherein enhancement of hepatic lipogenesis or fatty liver is mild or not recognized.

(2) An agent for suppressing body weight gain (for reducing body weight) or an anti-obesity agent according to the above (1) wherein the effective component is EPA-E.

(3) An agent for suppressing body weight gain (for reducing body weight) or an anti-obesity agent according to the above (1) or (2) wherein purity of the effective component is as high as at least 90% by weight.

(4) An agent for suppressing body weight gain (for reducing body weight) or an anti-obesity agent according to any one of the above (1) to (3) wherein the agent comprises an effective dose or amount of the effective component for suppressing increase of the CETP activity and/or LDL-C level.

(5) An agent for suppressing body weight gain (for reducing body weight) or an anti-obesity agent according to any one of the above (1) to (4) wherein the agent is substantially free from DHA or pharmaceutically acceptable salts, esters, and derivatives thereof.

(6) An agent for suppressing body weight gain (for reducing body weight) or an anti-obesity agent according to any one of the above (1) to (5) wherein the obesity is induced by intake of high fat diet, and in particular, induced by continuous intake of high fat diet.

(7) An agent for suppressing body weight gain (for reducing body weight) or an anti-obesity agent comprising at least one member selected from EPA and pharmaceutically acceptable salts, esters, and derivatives thereof as its effective component, for combined administration with at least one compound selected from the CETP inhibitors which is a second effective component.

(8) An agent for suppressing body weight gain (for reducing body weight) or an anti-obesity agent according to any one of the (1) to (7) wherein the agent also contains at least one CETP inhibitor as its second effective component.

(9) An agent for suppressing body weight gain (for reducing body weight) or an anti-obesity agent according to any one of the (1) to (8) wherein the CETP inhibitor is dalcetrapib or anacetrapib.

(10) A method for suppressing body weight gain, reducing body weight, or preventing, alleviating, or treating obesity comprising the step of administering an agent for suppressing body weight gain (for reducing body weight) or an anti-obesity agent comprising at least one member selected from EPA and pharmaceutically acceptable salts, esters, and derivatives thereof as its effective component to a patient suffering from obesity, and in particular, obesity of a type wherein enhancement of hepatic lipogenesis or fatty liver is mild or preferably not recognized.

(11) A method for suppressing body weight gain, reducing body weight, or preventing, alleviating, or treating obesity according to the above (10) wherein the effective component is EPA-E.

(12) A method for suppressing body weight gain, reducing body weight, or preventing, alleviating, or treating obesity according to the above (10) or (11) wherein purity of the effective component is 90% or higher by weight.

(13) A method for suppressing body weight gain, reducing body weight, or preventing, alleviating, or treating obesity according to any one of the above (10) to (12) wherein the effective component is administered at a dose effective for suppressing increase of the CETP activity and/or LDL-C level.

(14) A method for suppressing body weight gain, reducing body weight, or preventing, alleviating, or treating obesity according to any one of the above (10) to (13) wherein the agent is substantially free from DHA or pharmaceutically acceptable salts, esters, and derivatives thereof.

(15) A method for suppressing body weight gain, reducing body weight, or preventing, alleviating, or treating obesity according to any one of the above (10) to (14) wherein the obesity is induced by intake of high fat diet, and in particular, induced by continuous intake of high fat diet.

(16) A method for suppressing body weight gain, reducing body weight, or preventing, alleviating, or treating obesity comprising at least one member selected from EPA and pharmaceutically acceptable salts, esters, and derivatives thereof as its effective component, for combined administration with at least one compound selected from the CETP inhibitors which is a second effective component.

(17) A method for suppressing body weight gain, reducing body weight, or preventing, alleviating, or treating obesity according to any one of the above (10) to (16) comprising the step of administering a blended drug comprising at least one member selected from EPA and pharmaceutically acceptable salts, esters, and derivatives thereof as its first effective component and at least one CETP inhibitor as its second effective component.

(18) A method for suppressing body weight gain, reducing body weight, or preventing, alleviating, or treating obesity according to any one of the above (10) to (17) wherein the CETP inhibitor is dalcetrapib or anacetrapib.

(19) An additive for functional food, health food, designated health food, enteral nutritional food, diet food, or food supplement for suppressing body weight gain, reducing body weight, or preventing, alleviating, or treating obesity, or other functional food, health food, designated health food, enteral nutritional food, diet food, or food supplement wherein the additive is for obesity, and in particular, for the obesity of a type wherein enhancement of hepatic lipogenesis or fatty liver is mild or preferably not recognized, and the additive comprises at least one member selected from EPA and pharmaceutically acceptable salts, esters, and derivatives thereof as its effective component.

Advantageous Effects of Invention

Use of the at least one member selected from EPA and pharmaceutically acceptable salts, esters, and derivatives thereof has enabled to provide an agent for suppressing body weight gain (for reducing body weight) or an anti-obesity agent for the obesity of the type wherein enhancement of hepatic lipogenesis or fatty liver is mild or not recognized.

The present invention provides an agent for suppressing body weight gain (agent for reducing body weight) or an anti-obesity agent which has an extremely high effectiveness. More specifically, the body weight gain and the obesity are expected to be suppressed even in the case of continued intake of a high fat diet by the intake of the EPA of the present invention.

The most remarkable merit of the administration of the EPA in the present invention is the marked action of suppressing the body weight gain (reducing the body weight) compared to the cases of the intake of high fat diet with DHA or the intake of the ordinary diet. This is the merit which has never been recognized. This means that the suppression of the body weight gain (decrease of body weight) can be realized without depending on the intake of the low calorie diet or the low fat diet, namely, without reducing the dietary calory value.

Furthermore, the EPA of the present invention is expected to prevent lifestyle diseases (for example, dyslipidemia) which are highly likely to be induced by the body weight gain or the obesity, and prevent or improve diseases and symptoms related to the fat accumulation. More specifically, the EPA of the present invention is expected to exhibit the effect of alleviating or treating the lifestyle diseases through the improvement of plasma lipid markers such as total blood cholesterol (hereinafter abbreviated as "TC"), triglyceride (hereinafter abbreviated as "TG"), LDL-C, high-density lipoprotein cholesterol (hereinafter abbreviated as "HDL-C"), and non-HDL-C, suppression of the increase of the CETP activity, or the like.

The EPA of the present invention has very low toxicity, and therefore, the EPA of the present invention is highly safe.

DESCRIPTION OF EMBODIMENTS

Figure 1:
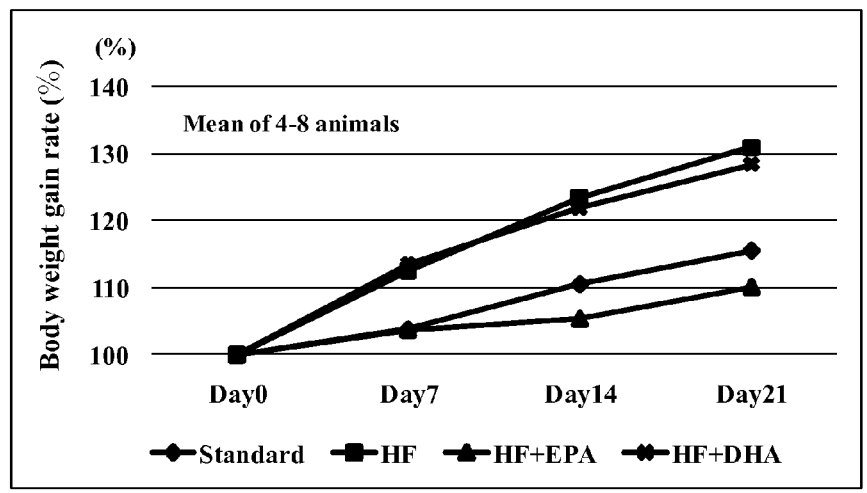
FIG. 1 is a bar graph showing body weight gain rate when the hamster has been fed with a high fat diet (HF), a high fat diet+EPA-E (HF+EPA), a high fat diet+DHA-E (HF+DHA), or a standard diet (Standard).

Next, the present invention is described in detail.

The present invention relates to an agent for suppressing body weight gain (for reducing body weight) or an anti-obesity agent for the obesity of the type wherein enhancement of hepatic lipogenesis or fatty liver is light, and preferably not recognized, wherein the agent comprises at least one member selected from EPA and pharmaceutically acceptable salts, esters, and derivatives thereof as its active ingredient. The present invention also relates to a method for using such agent.

The present invention also relates to an agent for suppressing body weight gain (for reducing body weight) or an anti-obesity agent, wherein the agent comprises at least one member selected from EPA and pharmaceutically acceptable salts, esters, and derivatives thereof as its effective component, and the agent suppresses increase in the CETP activity and increase in the LDL-C level, and. The present invention also relates to a method for using such agent.

The EPA or the pharmaceutically acceptable salts, esters, and derivatives thereof which is the effective component of the agent for suppressing body weight gain (agent for reducing body weight) or the anti-obesity agent of the present invention may be used as a drug for combination with the CETP inhibitor (combination drug) or as a composition combining with the CETP inhibitor (blended drug).

In the present invention, the term "high fat diet" means the diet wherein content of the fat per weight is at least about 20%. Alternatively, the "high fat diet" may be defined in terms of the proportion of energy taken from the fat in the total metabolic energy (Kcal). For example, the "high fat diet" and similar terms used in the present invention mean the diet wherein the calory taken through the fat in the entire calory is at least about 40%. The high fat diet used in the present invention may also be a commercially available conventional animal food (such as pet food) which is available as a normal fat diet, controlled diet, high fat diet, active diet, or functional diet.

In the present invention, the term "high-fat and high-sugar diet" means the diet wherein content of the fat per weight is at least about 20% and content of the sugar per weight is at least about 30%. The high-fat and high-sugar diet used in the present invention may also be a commercially available conventional animal food (such as pet food) which is available as a normal fat diet, controlled diet, high fat diet, high-fat and high-sugar diet, active diet, or functional diet.

The term "continuous intake of the high fat diet" means continuous intake of the diet having a fat content by weight of at least about 20% 3 times a day for at least 21 days. However, this term also includes the cases of continuous intake of the diet having a fat content by weight of at least about 20% once a day for at least 60 days as well as non-continuous intake of such diet for at least 60 days within 6 months.

In the present invention, the term "obesity" means the condition of excessive accumulation of the adipose tissue. When defined by BMI, "obesity" is the condition in which the BMI is at least 25, more preferably at least 30, and still more preferably at least 35. BMI is used as an index for measuring risk of a disease. In determining BMI, the body weight (kg) is divided with the square of body height (m) to thereby obtain the BMI ($kg/m^2$).

The obesity is divided into two categories by the type of the cause, namely, essential obesity (simple obesity) and symptomatic obesity. The obesity is also divided by the type of fat accumulation, namely, subcutaneous fat-type obesity (peripheral obesity) and abdominal visceral fat-type obesity (central obesity).

The "obesity" in the present invention is not particularly limited, and includes all of the obesity as described above.

In the present invention, the term "fatty liver" means the condition of excessive accumulation of fat (and in particular, triglyceride) in liver, and in particular, in the hepatocytes. In the field of medicine, the term "fatty liver" is defined as the state wherein fat vacuole is found in at least 30% of the hepatocyte. The liver forms triglyceride from the absorbed nutrients and a part of the triglyceride is stored in the hepatocyte, and therefore, healthy liver also contains 3 to 5% of the fat. However, excessive fat is accumulated in the liver as a result of various causes, and the case wherein 10% by weight or more of fat is present in the hepatocyte is also called the fatty liver. In the case of the "fatty liver", abnormal increase of lipid droplets (spherical fat) in the hepatocyte is confirmed by the microscopic observation of the fatty liver tissue, and it has been pointed out that lipid droplets are found in ⅓ or more of the hepatocytes.

In the present invention, the term that "fatty liver is mild" means the condition in which the lipid vacuole is observed in up to 30%, preferably up to 20%, and still more preferably up to 10% of the hepatocytes. The term that "fatty liver is mild" also means the condition in which the fat content in the hepatocytes is up to 10% by weight, and preferably up to 8% by weight, and also, the condition in which the lipid droplet is found only in up to ⅓, preferably up to ⅕, and more preferably up to 1/10 of the hepatocytes. Still further, the term that "fatty liver is mild" also includes the case in which liver infiltration (mottled fatty liver) is widely observed in an ultrasound (echo) image.

The fatty liver is not associated with clear somatic symptoms, and the fatty liver is often accidentally found in health examination, blood test, or the like where a liver disorder is found. The fatty liver is associated with high values of liver function test such as aspartate aminotransferase (AST (GOT)), alanine aminotransferase (ALT (GOT)), and the like. However, unlike other liver diseases, the fatty liver does not have characteristic pattern, and the fatty liver is not diagnosed solely by the abnormal test value. In abdominal ultrasound (echo), the fatty liver is whiter than the normal liver. Liver is in contact with the right kidney, and while black and white contrast (hepato-renal echo contrast) of the liver and the right kidney is normally similar, clear hepato-renal echo contrast is found in the case of the fatty liver. The fatty liver is diagnosed by combining this result with the observation of the blood vessels in the liver.

In the present invention, the term "pharmaceutically acceptable" means that the particular substance or composition is chemically and/or toxicologically compatible with other components in the formula and/or the mammal which is treated with the formula.

In the present invention, the term "therapeutically effective amount" means the amount of compound capable of (i) treating or preventing particular disease, disorder, or dysfunction, (ii) alleviating, improving, or solving of at least one symptom of the particular disease, disorder, or dysfunction, or (iii) preventing or delaying the onset of at least one symptom of the particular disease, disorder, or dysfunction (for example, reducing the amount of intake or appetite).

In the present invention, the "test subject" of the administration of the agent for suppressing body weight gain (for reducing body weight) and/or the anti-obesity agent of the present invention is not particularly limited, and exemplary subjects include human, farming (agricultural) animals, domestic animals such as dog and cat, mouse, rat, guinea pig, hamster, rabbit, and other mammals, preferably, human, hamster, rabbit, monkey, and other animals having CETP, and more preferably, human.

In the present invention, the term "treatment" or "therapy" means decrease in the seriousness of the relevant disease by reducing whole body weight or by reducing the amount of the fat.

In the present invention, the term "prevention" means prevention of the occurrence of the obesity (body weight gain), namely, administration of the compound of the present invention before the onset of the obesity condition. This means use of the compound of the present invention as a preventive drug to thereby prevent body weight gain, or to thereby prevent the disease which may be induced by the body weight gain.

EPA is all cis-5,8,11,14,17-icosapentaenoic acid which is an ω3 polyunsaturated fatty acid comprising 20 carbon atoms, and it has 5 carbon to carbon double bonds in the molecule with the first double bond being located at the third position from the side of the methyl group. Unless otherwise noted, the term "EPA" in the present invention may include not only the EPA but also its pharmaceutically acceptable salts, esters, and derivatives such as amides, phospholipids, and glycerides.

The EPA used in the present invention may be any of synthetic, semi-synthetic, and natural products, or any natural oil comprising such product. The term "natural product" includes the product extracted from an EPA-comprising natural oil by a method known in the art, such product which has undergone crude purification or further fine purification. The semi-synthetic product includes the polyunsaturated fatty acid produced by a microorganism or the like, and also, such polyunsaturated fatty acid or natural polyunsaturated fatty acid which has been chemically treated by esterification or transesterification. In the present invention, such EPA may be used alone or in combination of two or more kinds.

In the present invention, examples of the EPA include EPA; its pharmaceutically acceptable salts such as inorganic salts such as sodium salt and potassium salt, organic salts such as benzylamine salt and diethylamine salt, and salts with a basic amino acid such as arginine salt and lysine salt; and esters such as alkyl esters such as ethyl ester and other mono-, di-, and TG esters. The preferred is the ethyl ester, namely, EPA-E.

The EPA used is not particularly limited for its purity. The EPA, however, may preferably have an EPA content in the entire fatty acid of the composition of the present invention of at least 45% by weight, more preferably at least 70% by weight, still more preferably at least 85% by weight, still more preferably at least 90% by weight, even more preferably at least 95% by weight, and most preferably at least 96.5% by weight. In other words, the composition of the present invention may preferably have a higher EPA purity.

The composition of the present invention may also comprise ω3 polyunsaturated fatty acids other than the EPA such as DHA, docosapentaenoic acid (DPA), and α-linolenic acid; their pharmaceutically acceptable salt or ester. However, the fatty acid other than the EPA is preferably used at a low content, and in the case of DHA, the content is preferably less than 2% by weight, and more preferably less than 1% by weight. More preferably, the composition is substantially free from the DHA or the DHA is below the detectable level. In addition, content of the long chain unsaturated fatty acid, and in particular, content of the ω6 polyunsaturated fatty acid and especially arachidonic acid should be reduced preferably to the level of less than 2% by weight, and more preferably to the level of less than 1% by weight. More preferably, the composition is substantially free from the arachidonic acid, and the arachidonic acid is preferably below the detectable level. In the present invention, the terms "ω3 polyunsaturated fatty acid", "DHA", "DPA", and "α-linolenic acid" may be used, unless otherwise noted, in the meanings including not only the free fatty acid but also their pharmaceutically acceptable salts, esters, and derivatives such as amides, phospholipids, and glycerides.

Compared to the fish oil or the fish oil concentrate, the EPA-E used in the improvement or therapeutic agent of the present invention comprises impurities such as saturated fatty acids and arachidonic acid which are unfavorable for cardiovascular events at a lower content, and this enables realization of the intended action without causing the problems of excessive nutrition or excessive intake of the vitamin A. When the EPA-E in the form of ester is used, a sufficiently stable composition can be obtained by adding a commonly used antioxidant since the EPA-E in ester form has an oxidation stability higher than the fish oils which are mainly in TG form.

The EPA-E used may be a soft capsule containing the EPA-E at a high purity (at least 96.5% by weight) (product name, Epadel; manufactured by Mochida Pharmaceutical Co., Ltd.) available in Japan as a therapeutic agent for ASO (arteriosclerosis obliterans) and hyperlipidemia.

The embodiments of the use of the agent for suppressing body weight gain (for reducing body weight) or the anti-obesity agent of the present invention are not particularly limited as long as the agent is used in a way such that the therapeutic effects of the effective components, namely, at least one member selected from the group consisting of EPA and pharmaceutically acceptable salts, esters, and derivatives thereof are realized. Exemplary such embodiments include the embodiment wherein the EPA is solely used and the embodiment wherein the agent for suppressing body weight gain (for reducing body weight) or the anti-obesity agent comprises the EPA and one or more different effective components.

In the present invention, a CETP inhibitor, for example, compounds described in WO 1998/035937 (JAPAN TOBACCO INC.) and WO 2006/014357 (Merck & Co., Inc.) such as dalcetrapib or anacetrapib may be combined and/or blended as the second effective component.

In the present invention, "combined use" of the effective components means use of the effective components in combination, and it includes both the administration of the EPA and the second effective component as components in a blended drug comprising the EPA and the second effective component, and the administration of the EPA and the second effective component as separate preparations at the same timing or at different timing with a time lag. The embodiment of "the administration as separate preparations at the same timing or at different timing with a time lag" includes both (1) the embodiment in which the patient receiving the EPA is administered with another composition comprising the second effective component, and (2) the embodiment in which the patient receiving a composition comprising the second effective component is administered with a composition comprising the EPA as its effective component. The "combined use" may not necessarily mean that both effective components are simultaneously present in the patient's body, for example, in the patient's blood, and the term "combined use" used in the present invention designates the embodiment in which the composition comprising the other effective component is administered when the effect and/or action of one effective component is still being developed in the body of the patient, namely, the embodiment which realizes the alleviative or therapeutic effects of the dyslipidemia by using the alleviative or therapeutic drug of the present invention. The preferred is the embodiment in which both effective components are simultaneously present in the patient's body, for example, in the patients' blood, and also preferred is the embodiment in which the composition comprising the other effective component is administered within 24 hours after the administration of the composition comprising one effective component.

The embodiments of the combined use of the agent for suppressing body weight gain (for reducing body weight) or the anti-obesity agent of the present invention is not particularly limited as long as the effective components are used in combination, and examples of the combined use include the combined drug (combination drug) and the combined composition (blended drug) to be combined. Exemplary such embodiments of the drug administration include, for example, (1) administration of single preparation having both effective components incorporated therein; (2) administration of both effective components by preparing separate preparations each comprising different effective components, and simultaneously administering these separate preparations from the same administration route with or without producing a kit of the combination of two preparations; (3) administration of both effective components by preparing separate preparations each comprising different effective components, and administering these separate preparations from the same administration route at a different timing with a time lag from the same administration route with or without producing a kit of the combination of two preparations; (4) administration of both effective components by preparing separate preparations each comprising different effective components, and simultaneously administering these separate preparations from different administration routes (of the same patient from different sites) with or without producing a kit of the combination of two preparations; and (5) administration of both effective components by preparing separate preparations each comprising different effective components, and administering these separate preparations at different timing with a time lag from different administration routes (of the same patient from different sites) with or without producing a kit of the combination of two preparations.

When the effective components are administered at different timing with such time lag, the EPA and the second effective component may be administered in this order, or in the opposite order. When the effective components are administered simultaneously, these components may be mixed immediately before the administration if the administration route is the same, while the effective components may be separately administered, and the effective components may also be used deliberately at different timing for various purposes. In an exemplary embodiment, the drug comprising one effective component may be administered, and thereafter, the drug comprising another effective component may be administered when the effect of the first effective component is about to be developed or while the effect of the first effective component is still fully developed. In another embodiment, one drug comprising one effective component, and in particular, the drug comprising the second effective component may be administered once a day, and the drug comprising the other effective component, and in particular, the drug comprising the EPA may be administered two or more times, for example, two or three times a day, or alternatively, once a day as in the case of the EPA. When both drugs are administered once a day, and more preferably, when both drugs are administered once a day simultaneously, or administered by incorporating in a blended drug formulation, the burden of drug administration on the patients will be reduced to improve the drug compliance, and in turn, it is expected to improve the alleviative or therapeutic effects and reduce the side effect. It is also possible that both drugs are administered and the administration of one drug is withdrawn when the effects of the components are about to be developed or while the effects of the components are still fully developed. When the drug administration is withdrawn, the dose may be incrementally reduced, or alternatively, one drug may be administered during the washout period of the other drug.

The therapeutic effect is not limited as long as the effect is an action of suppressing the body weight gain (the action of reducing the body weight) or an anti-obesity action; improvement of biochemical markers or pathological conditions or a therapeutic effect related to dyslipidemia caused by the body weight gain or obesity; or suppression of the progress to metabolic syndrome, cardiocerebrovascular event, or limb peripheral ulcer or gangrene, and an exemplary such effect is improvement in the concentration of a lipid marker in the plasma. Exemplary lipid markers in the plasma include TC, TG, LDL-C, HDL-Cho, very low density lipoprotein cholesterol (hereinafter abbreviated as "VLDL-C"), non-HDL-C, intermediate density lipoprotein cholesterol (IDL-C), very high density lipoprotein cholesterol (VHDL-C), free fatty acid, phospholipid, chylomicron, apolipoprotein B (ApoB), lipoprotein (a) (Lp(a)), remnant-like lipoprotein cholesterol (RLP-C), and small, dense low density lipoprotein cholesterol (sdLDL-C). Among these, the most important therapeutic effect is suppression of the increase in the LDL-C level. The improvement or the therapeutic effect may be monitored by other biochemical, pathological, or pathologic parameters related to the dyslipidemia.

The dose and dosage period of the EPA used in the alleviating or therapeutic agent of the present invention may be the dose and the period sufficient for the development of the intended action. Such dose and dosage period may be adequately adjusted depending on the dosage form, administration route, administration frequency per day, seriousness of the symptom, body weight, age, and the like. In the case of oral administration, the drug may be administered, for example, at 0.1 to 5 g/day, preferably 0.2 to 3 g/day, more preferably 0.4 to 1.8 g/day, and more preferably 0.6 to 0.9 g/day in terms of EPA-E in one to three doses. If necessary, the entire dose may be administered in one dose or in several divided doses.

The EPA of the present invention may be added at an amount of about 1 to 2% in the high fat diet to thereby suppress the body weight gain (or reduce the body weight) induced by the intake of the high fat diet and/or suppress the increase of CETP activity and suppress the increase of LDL-C level. Alternatively, the agent for suppressing body weight gain (agent for reducing body weight) or the anti-obesity agent of the present invention may be simultaneously administered with the intake of the high fat diet so that EPA would be at an amount of about 1 to 2% in relation to the high fat diet.

Absorption of the EPA-E is influenced by the diet, and therefore, the agent is preferably administered during the meal or after the meal, and more preferably, immediately after the meal (within 30 minutes). In view of improving the absorptivity, the agent may also be administered in the form of emulsion, or alternatively, combined with a bile acid derivative such as ursodeoxycholic acid, chenodeoxycholic acid, bile powder, deoxycholic acid, cholic acid, bile extract, bear bile, oriental bezoar, or dehydrocholic acid. Absorptivity of the EPA-E will be improved when administered in the form of an emulsion or a self-emulsifying preparation, or in combination with a bile acid derivative, and merit of the present invention can be realized even when administered, for example, before or immediately before the meal or before going to bed, namely, at a timing other than during, after, or immediately after the meal, even if administered to a patient with reduced intestinal absorptive power (for example, elderly, patient of intestinal disease, patient after the intestinal surgery, patient of end-stage cancer, or patient taking a lipase inhibitor), or even if administered at a reduced dose.

When EPA in the dose as described above is orally administered, the period of the administration is preferably 1 year, more preferably 2 years, still more preferably 3.5 years, and even more preferably 5 years although the administration period is not particularly limited. The administration, however, is preferably continued as long as the patient still suffers from the obesity of the type wherein the enhancement of hepatic lipogenesis or the fatty liver is mild or not recognized, the value of the pathological or biochemical index related to the dyslipidemia or peripheral vascular insufficiency is still abnormal, or the risk of the onset and/or recurrence of dyslipidemia or the associated peripheral blood circulation disorder is still high. In addition, the agent may also be administered, for example, every other day, 2 to 3 days in 1 week, or in some instance, after a drug withdrawal period of approximately 1 day to 3 months, or preferably approximately 1 week to 1 month.

Japan Atherosclerosis Society adopts an LDL-C level (dyslipidemia at a value higher than 140 mg/dL) and HDL-C value (dyslipidemia at a value higher than 40 mg/dL) for the "diagnostic criteria of the dyslipidemia", and lays emphasis on the importance of LDL-C level for the diagnostic criteria in the screening of the group with a high risk of atherosclerotic disease. Strong relation between the hypercholesterolemia or the hyper-LDL-cholesterolemia with the vascular disorder such as coronary artery diseases or cerebral infarction has been demonstrated, and therefore, these diseases can be prevented by treating the hyper-LDL-cholesterolemia (Guideline for Prevention of Atherosclerotic Cardiovascular Diseases, Japan Atherosclerosis Society, 2007).

Continuous intake of a high fat diet is likely to invite not only increase in the body weight gain, but also, worsening of the plasma lipid markers (TC, TG, LDL-C, HDL-C, and the like).

There has been no report that continuous intake of the high fat diet with the intake of EPA or other ω3 unsaturated fatty acids suppresses the body weight gain (reduces the body weight) simultaneously with the suppressing of the increase of the LDL-C level. On the contrary, there is a report that administration of a fish oil results in the increase of LDL-C level with no change in the body weight (The Journal of Lipid Research, vol. 33, pp. 263-271, 1992).

The at least one member selected from EPA and pharmaceutically acceptable salts, esters, and derivatives thereof of the present invention suppresses the body weight gain (reduces the body weight), and also, it suppresses increase of the LDL-C level. Accordingly, use of an agent for suppressing body weight gain (agent for reducing body weight) or an anti-obesity agent comprising at least one member selected from EPA and pharmaceutically acceptable salts, esters, and derivatives thereof as its effective component for obesity, and in particular, for the obesity of the type wherein enhancement of hepatic lipogenesis or fatty liver is mild or preferably not recognized, induced by continuous intake of the high fat diet, enables not only the suppression of the body weight gain (anti-obesity), but also prevention of the diseases caused by the hyper-LDL-cholesterolemia, for example, vascular disorders such as coronary artery disease or cerebral infarction by the suppression of increase of the LDL-C level.

While decrease in the HDL-C value is one of the major risk factors of the coronary heart disease, there is not yet a therapy capable of sufficiently increasing the HDL-C value. It has been recently reported that inhibition of the CETP results in the increase of the HDL-C value, and various investigations on the CETP inhibitor are being conducted. CETP is a glycoprotein mainly produced in liver and small intestine, and it has the function of transferring the cholesterol ester in HDL-C to VLDL-C and LDL-C. HDL-C increases by the alcohol drinking, exercise, and other environmental factors, and these are associated with decrease in the CETP activity and complete lack of the CETP in the case of gene abnormality induces serious hyper HDL-C cholesterolemia. Accordingly, CETP is conceivably involved in the increase of the HDL-C.

Combined use of the agent for suppressing body weight gain (agent for reducing body weight) or the anti-obesity agent which is the at least one member selected from EPA and pharmaceutically acceptable salts, esters, and derivatives thereof of the present invention with the CETP inhibitor is expected to have the action of increasing the HDL-C value simultaneously with the action of suppressing the increase of the LDL-C level even in the continuous intake of the high fat diet. Because of such synergistic effect, its use for the prevention and alleviation of the metabolic syndrome such as dyslipidemia, hypertension, arteriosclerosis, diabetes, and obesity is expected.

In addition, since EPA has the action of suppressing the increase of the CETP activity, combined use of the EPA with a CETP inhibitor is expected to have the synergetic effect with the CETP inhibitor or the effect of enhancing the CETP inhibitor in the action of suppressing the body weight gain (reducing the body weight) or the anti-obesity action or the action of reducing the LDL-C. The combined use of the EPA with a CETP inhibitor is also expected to enable decrease in the dose of the CETP inhibitor, and hence, alleviation of the side effects of the CETP inhibitor.

In administering the agent for suppressing body weight gain (for reducing body weight) or the anti-obesity agent of the present invention, the effective components may be administered either as-prepared compounds (which may comprise inevitable components remaining after the purification), or after preparing into an adequate medical preparation by suitably combining with an adequate carrier, medium, excipient, binder, lubricant, colorant, flavor, or optional additives such as sterilized water, vegetable oil, non-toxic organic solvent, non-toxic solubilizing agent (for example, glycerin or propylene glycol), emulsifier, suspending agent (for example, Tween 80 or gum arabic solution), isotonic agent, pH adjusting agent, stabilizer, soothing agent, corrective, flavoring agent, preservative, antioxidant, buffer, colorant, or absorption enhancer commonly used in the art. Specific examples of the additive include lactose, partially pregelatinized starch, hydroxypropyl cellulose, macrogol, tocopherol, hydrogenated oil, sucrose fatty ester, hydroxypropyl methylcellulose, titanium oxide, talc, dimethylpolysiloxane, silicon dioxide, carnauba wax, and sodium deoxycholate.

More specifically, since EPA is highly unsaturated, effective amount of an oil-soluble antioxidant, for example, at least one member selected from butylated hydroxytoluene, butylated hydroxyanisole, propyl gallate, propyl gallate, pharmaceutically acceptable quinone, astaxanthin, and α-tocopherol is preferably incorporated in the composition. The emulsion comprising water is highly vulnerable to oxidation, and the emulsion with smaller emulsion droplet diameter is more vulnerable to oxidation, and accordingly, incorporation of a water-soluble antioxidant and/or an oil-soluble antioxidant at an amount effective for the oxidation inhibition is preferable, and simultaneous incorporation of water-soluble and oil-soluble antioxidants is even more preferable. Exemplary water-soluble antioxidants include ascorbic acid and its derivatives, erythorbic acid and its derivatives, nitrite, and citric acid, and exemplary oil-soluble antioxidants include butylated hydroxytoluene, butylated hydroxyanisole, propyl gallate, propyl gallate, pharmaceutically acceptable quinone, astaxanthin, and α-tocopherol is preferably incorporated in the composition. In addition, the emulsified composition prepared is preferably sealed and stored in a vessel purged with nitrogen. Storage temperature is preferably room temperature, and the more preferred is the storage in cool and dark place. However, frozen storage is preferably avoided since the freezing may result in the loss of emulsion stability.

The dosage form of the preparation is not particularly limited since the dosage form may differ by the way how the effective components of the present invention are combined. Exemplary dosage forms in the case of oral preparation include tablet, film coated tablet, capsule, microcapsule, granules, fine granules, powder, self-emulsifying preparation, oral liquid preparation, syrup, jelly, and inhalant, and exemplary dosage forms for parenteral preparation include ointment, suppository, injection (emulsion, suspension, or non-aqueous) or solid injection which is emulsified or suspended before use, infusion, and external medicine, for example, for percutaneous absorption. While the drug may be administered orally, intravenously, intraarterially, by inhalation, rectally, intravaginally, or by external administration, oral dosage form is desirable when oral administration is possible in view of the administration convenience, and the preferred are the oral administration by capsule such as soft capsule or microcapsule having the drug incorporated therein and the administration by way of tablet or film coated tablet. Oral administration by using an enteric-coated preparation or extended release preparation is also preferable, and use of jelly for oral administration is also preferable for patients undergoing dialysis or patients suffering from aphagia.

The agent for suppressing body weight gain (for reducing body weight) or the anti-obesity agent of the present invention may be used in combination with or may be a blended drug blending the second effective component in the same drug. In the case of combined use, namely, in the case of using the agent for suppressing body weight gain (agent for reducing body weight) or the anti-obesity agent of the present invention in combination with the drug comprising the second effective component, each drug may be prepared by a method known in the art.

The second effective component is not particularly limited as long as the merit of the present invention is not adversely affected. CETP inhibitor, for example, compounds described in WO1998/035937 (JAPAN TOBACCO INC.) and WO2006/014357 (Merck & Co., Inc.) such as dalcetrapib or anacetrapib may be combined and/or blended as the second effective component.

The second drug used in combination with or by blending with the agent for suppressing body weight gain (for reducing body weight) or the anti-obesity agent of the present invention is preferably used according to the administration procedure and the dose recommended for the sole use of the particular drug, and the type, dosage form, administration route, and administration frequency per day may be adequately adjusted depending on the severity of the symptoms, body weight, age, gender, and the like. When orally administered, the additional drug is typically administered at a dose of about 0.001 mg to about 100 mg/day, and preferably about 0.1 mg to about 10 mg/day per 1 kg of body weight in a single dose to three divided doses. If necessary, total dose may be administered in several divided doses.

The blended drug is not particularly limited for its dosage form, and it may be administered in the form of an oral preparation such as tablet, film coated tablet, capsule, microcapsule, granules, fine granules, powder, self-emulsifying preparation, oral liquid preparation, syrup, or jelly, or in the form of parenteral preparations such as injection, infusion, percutaneous absorptive preparation, or other external medicine. The blended drug may also be an extended release preparation, or a preparation in which the two components are released at different timing.

The blended drug of the present invention may comprise a pharmaceutically acceptable excipient in addition to the effective components, and any known antioxidant, coating agent, gelation agent, corrective, flavoring agent, preservative, emulsifier, pH adjusting agent, buffer, colorant, or the like may be incorporated as required. Preferable dosage form and excipients in the case of the blended drug are the same as those of the combined use of separate drugs as described above.

The blended drug of the present invention may be prepared by a method commonly used in the art. More specifically, the EPA in the form of powder may be prepared, for example, by drying an oil-in-water emulsion comprising (A) EPA-E, (B) a dietary fiber, (C) a starch hydrolysate and/or a hydrolysate of low sugar reduced starch, and (D) a water-soluble antioxidant under high vacuum, and pulverizing the dried product (JP 10-99046 A). This powder EPA-E and a powder of nicotinic acid or its pharmaceutically acceptable derivative may be used in a method commonly used in the art to obtain granules, fine granules, powder, tablet, film-coated tablet, chewable tablet, controlled-release tablet, or orally disintegrating tablet (OD tablet).

A chewable tablet may be obtained by a method known in the art, for example, by emulsifying EPA-E in a solution of water-soluble polymer such as hydroxypropylmethylcellulose, and spraying the resulting emulsion onto an additive such as lactose to obtain powdery particles (see JP 8-157362 A), and then, mixing the powder with a powder of nicotinic acid derivative, and pressing the tablets.

A controlled-release tablet may be prepared, for example, by preparing (1) a tablet having one of the EPA-E and the nicotinic acid derivative as an interior layer and the other component in the exterior layer, (2) a tablet wherein a disk matrix comprising one component is disposed over another disk matrix comprising the other component, (3) a tablet having a particulate capsule containing one component embedded in the matrix comprising the other component, and (4) a tablet wherein some means of controlled-release is provided after preliminarily mixing both components. Each effective component is preferably released at a controlled rate, and they may be released either simultaneously or separately at a different timing.

An orally disintegrating tablet may be prepared, for example, by a known method such as the technology described in JP 8-333243 A, and an oral film preparation may be prepared, for example, by a known method such as the technology described in JP 2005-21124 A. When a preparation such as a soft capsule or a liquid preparation is prepared from a nicotinic acid derivative which is not easily soluble in the EPA, the techniques as described above are necessary. The blended drug of the present invention also includes such preparation wherein the EPA and the nicotinic acid derivative are blended in one drug.

The blended drug of the present invention is preferably released and absorbed in a manner enabling the development of the pharmacological action of the effective component. The blended drug of the present invention preferably exhibits at least one effect selected from excellent releasability of the effective component, excellent absorbability of the effective component, excellent dispersibility of the effective component, storage stability of the blended drug, ease of intake by the patient, and compliance.

The agent for suppressing body weight gain (for reducing body weight) or the anti-obesity agent of the present invention comprising at least one member selected from EPA and pharmaceutically acceptable salts, esters, and derivatives thereof as its effective component is also effective in alleviating, treating, or secondarily preventing dyslipidemia or suppressing the progress to metabolic syndrome, cardiocerebrovascular events, limb peripheral ulcer or gangrene in animals, and in particular, mammals. Exemplary mammals include human, domestic animals such as cattle, horse, pig, and companion animals such as dog, cat, rabbit, rat, and mouse, and the preferred is human. The agent of the present invention is expected to exhibit the effects of suppressing the body weight gain (reducing body weight) with synergistic alleviation or therapeutic effects for the dyslipidemia in dyslipidemia patients exhibiting increased blood lipid, insulin resistance, or increased blood pressure, such as the patients of metabolic syndrome.

By preparing a blended drug or a kit with the second effective component, the burden of the drug administration on the patient may be reduced and the drug compliance may be improved to thereby enhance effects of alleviation or treatment.

The EPA-E or the like is already used in the field of foods. The agent for suppressing body weight gain (for reducing body weight) or the anti-obesity agent or the like of the present invention may also be used for various foods such as functional food, health food, designated health food, diet food, food supplement, or enteral nutritional food, as well as additives for these foods.

Example 1

Next, the present invention is described in detail which by no means limits the scope of the invention.
(Hamster)

6 week old male Syrian hamsters (Japan SLC, Inc.) were bred at a temperature of 23±3° C. and a light-dark cycle of 12 hours on a free feeding of standard diet for 11 days, and the hamsters were divided into 4 groups, namely, standard forage group (Standard) (n=4), high-fat diet group (n=8), EPA group (HF+EPA-E) (n=8), and DHA group (HF+DHA-E) (n=7).
(Breeding Diet (% by Weight))

The standard diet used was CLEA Rodent Diet CE-2 (4.8% fat) manufactured by CLEA Japan, Inc. and the high fat diet (HF) used was Hypercholesterolemic Hamster Diet (9% sugar and fat 21% fat) manufactured by Wilson.

Experimental Example 1

Effect of Suppressing the Body Weight Gain in the Obesity Model Hamster Fed on a High Fat Diet The effects of the EPA and DHA on the body weight gain were confirmed by using hamsters fed on a high fat diet (HF).

During the feeding on the high fat diet, a mixed diet of high fat diet+2% EPA-E (comprising 98.24% EPA-E manufactured by Nippon Suisan Kaisha, Ltd.) was given to the EPA group, and a mixed diet of high fat diet+2% DHA-E (comprising 97.4% DHA-E manufactured by Equateq Ltd.) was given to the DHA group (with the diet changed once a day in the morning). The control group was given a high fat diet or a standard diet (comprising 4.8% fat) (with the diet changed once a day in the morning). The body weight was measured from the day of the start of the administration. The body weight gain rate on the 21st day was higher in the group fed on the high-fat diet group compared to the standard forage group, and the group fed on the high-fat diet was in the condition of obesity. The EPA group exhibited the body weight gain rate on the 21st day lower than the control high-fat diet group, and the level of the body weight gain rate of the EPA group did not exceed the standard forage group demonstrating marked action of suppressing the body weight gain (or reducing the body weight). On the other hand, the body weight gain rate of the DHA group was higher than that of the standard forage group, and the level of the body weight gain rate of the DHA group was approximately equal to that of the high-fat diet group, and the action of suppressing the body weight gain was not confirmed. These results demonstrate the useful action of the EPA that it can suppress the body weight gain (obesity) that could not be suppressed by the DHA (FIG. 1). With regard to the observation of the liver of the hamster, clear fatty liver was not found in any of these groups.

It is to be noted that significant difference was not recognized in the daily dietary intake (in terms of energy) between the high-fat diet group, the EPA group, and the DHA group.

These results confirmed the action of suppressing the body weight gain (or reducing the body weight) or the anti-obesity action of the EPA-E for the obesity, and in particular, for the obesity with no finding of the enhancement of the hepatic lipogenesis or with no fatty liver.

Figure 2:
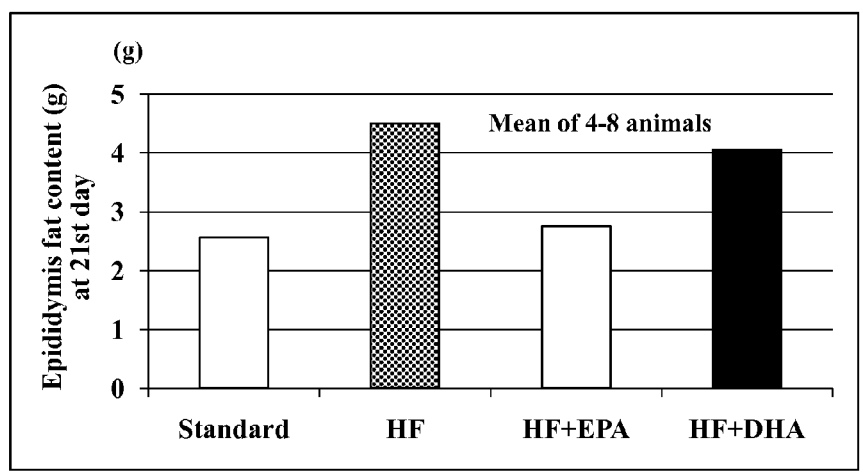
FIG. 2 is a bar graph showing epididymal fat content (mean of 4 to 8 animals) on the 21st day when the hamster has been fed with a high fat diet (HF), a high fat diet+EPA-E (HF+EPA), a high fat diet+DHA-E (HF+DHA), or a standard diet (Standard).

The amount of fat in the epididymis on the 21st day was also measured for each group (FIG. 2), and the results confirmed that increase in the amount of fat was significantly suppressed in the EPA group. This confirms that the action of suppressing the body weight gain (or reducing the body weight) of the EPA-E is realized by the action of suppressing (or reducing) the amount of fat, namely, the anti-obesity action.

Experimental Example 2

Effects on LDL-C Level in High Fat Diet Hamster

The action of the EPA and the DHA on the LDL-C level was confirmed by using the hamsters fed on a high fat diet.

Figure 3:
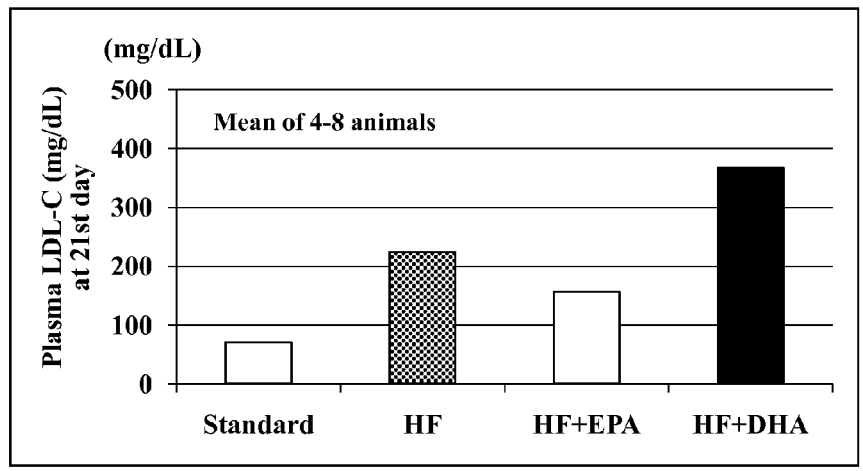
FIG. 3 is a bar graph showing LDL-C level (mean of 4 to 8 animals) on the 21st day when the hamster has been fed with a high fat diet (HF), a high fat diet+EPA-E (HF+EPA), a high fat diet+DHA-E (HF+DHA), or a standard diet (Standard).

Along with the experiment of the action of suppressing the body weight gain in Experimental Example 1, blood was collected at day 7, 14, and 21 after the starting of the administration, and plasma was separated by centrifugation. Plasma LDL-C concentration was measured by using a commercially available test reagent (Wako L-Type LDL-C manufactured by Wako Pure Chemical Industries). The plasma LDL-C concentration on the 21st day of the administration is shown in FIG. 3.

An action of increasing the plasma LDL-C level was found in the high-fat diet group and the DHA group. Compared to these two groups, an action of suppressing the increase of the plasma LDL-C level was found in the EPA group.

Experimental Example 3

Effects on CETP Activity Value in High Fat Diet Hamster

The action of the EPA and the DHA on the CETP activity value was confirmed by using the hamsters fed on a high fat diet.

Figure 4:
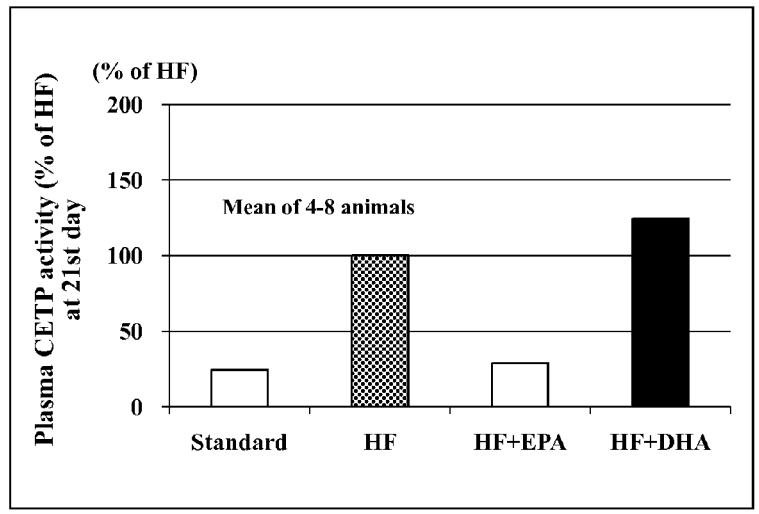
FIG. 4 is a bar graph showing the CETP activity value (mean of 4 to 8 animals) on the 21st day when the hamster has been fed with a high fat diet (HF), a high fat diet+EPA-E (HF+EPA), a high fat diet+DHA-E (HF+DHA), or a standard diet (Standard). The activity value of each group was calculated by using the activity value of the case of the high fat diet (HF) for the standard.

Along with the experiment of the action of suppressing the body weight gain in Experimental Example 1, blood was collected at day 7, 14, and 21 after the starting of the administration, and plasma was separated by centrifugation. Plasma CETP activity value was measured by using a test reagent (CETP activity assay kit manufactured by Bio Vision). The CETP activity value on the 21st day of the administration is shown in FIG. 4.

In the high-fat diet group and the DHA group, increase in the CETP activity was confirmed. In contrast, the action of suppressing the increase of the CETP activity was confirmed in the EPA group.

Experimental Example 4

Correlation of LDL-C Level and CETP Activity Value in High Fat Diet Hamster

Figure 5:
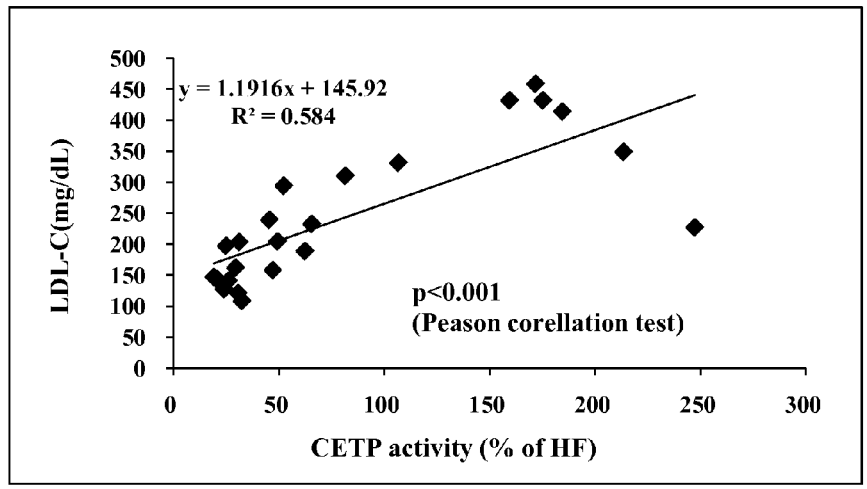
FIG. 5 is a correlation diagram of the LDL-C level and the CETP activity value on the 21st day when the hamster has been fed with a high fat diet (HF), a high fat die+EPA-E (HF+EPA), a high fat diet+DHA-E (HF+DHA), or a standard diet (Standard).

Correlation diagram of the LDL-C level and the CETP activity value is shown in FIG. 5. As shown in FIG. 5, a very good correlation between the LDL-C level and the CETP activity value was observed in the administration of the EPA-E to the hamster fed on the high fat diet. Conceivably, intake of the EPA-E suppressed increase in the CETP activity, and hence, suppressed increase in the LDL-C level. Accordingly, combined use of the EPA-E with the CETP inhibitor is expected to synergetically reduce the LDL-C level. In contrast with the normally observed worsening of the plasma lipid marker value in the continuous intake of the high fat diet, the intake of the EPA-E suppressed worsening of plasma lipid marker value. As described above, the agent for suppressing body weight gain (agent for reducing body weight) or an anti-obesity agent of the present invention is useful since it is expected to show the alleviative action for the dyslipidemia even in the continuous intake of the high fat diet.

The invention claimed is:

1. A method for suppressing body weight gain, reducing body weight, or preventing, alleviating, or treating obesity of a mammal having cholesteryl ester transforming protein (CETP) comprising the step of:
administering a composition comprising:
an agent for suppressing body weight gain or reducing body weight, or an anti-obesity agent containing at least one member selected from the group consisting of EPA, a pharmaceutically acceptable salt thereof, an ester thereof, and a derivative thereof as its effective component,
less than 2% by weight of at least one member selected from the group consisting of docosahexaenoic acid (DHA), a pharmaceutically acceptable salt thereof, an ester thereof, and a derivative thereof, and
less than 2% by weight of a long chain unsaturated fatty acid of arachidonic acid,
to a patient suffering from obesity, or obesity of a type wherein enhancement of hepatic lipogenesis or fatty liver is mild, the patient being a mammal having CETP,
wherein a content of said EPA, pharmaceutically acceptable salt thereof, ester therof, and derivative thereof in an entire fatty acid content of the composition is at least 45% by weight.

2. The method for suppressing body weight gain, reducing body weight, or preventing, alleviating, or treating obesity of a mammal having CETP according to claim 1, wherein the effective component is ethyl icosapentate (EPA-E).

3. The method for suppressing body weight gain, reducing body weight, or preventing, alleviating, or treating obesity according to claim 1, wherein purity of the effective component is as high as 90% by weight or more.

4. The method for suppressing body weight gain, reducing body weight, or preventing, alleviating, or treating obesity of a mammal having CETP according to claim 1, wherein the effective component is administered at an effective dose for suppressing increase of (i) cholesteryl ester transfer protein (CETP) activity, (ii) low-density lipoprotein Cholesterol (LDL-C) level, or (iii) CETP activity and LDL-C level.

5. The method for suppressing body weight gain, reducing body weight, or preventing, alleviating, or treating obesity of a mammal having CETP according to claim 1, wherein the agent is free from DHA, a pharmaceutically acceptable salt thereof, an ester thereof, or a derivative thereof.

6. The method for suppressing body weight gain, reducing body weight, or preventing, alleviating, or treating obesity of a mammal having CETP according to claim 1, wherein the obesity is induced by intake of high fat diet.

7. The method for suppressing body weight gain, reducing body weight, or preventing, alleviating, or treating obesity of a mammal having CETP according to claim 1, comprising the step of administering a blended drug containing at least one member selected from EPA, a pharmaceutically acceptable salt thereof, an ester thereof, and a derivative thereof as its first effective component and at least one cholesteryl ester transfer protein (CETP) inhibitor as its second effective component.

8. The method for suppressing body weight gain, reducing body weight, or preventing, alleviating, or treating obesity of a mammal having CETP according to claim 7, wherein the cholesteryl ester transfer protein (CETP) inhibitor is dalcetrapib or anacetrapib.

9. The method for suppressing body weight gain, reducing body weight, or preventing, alleviating, or treating obesity of a mammal having CETP according to claim 2, wherein purity of EPA-E is as high as 90% by weight or more.

10. The method for suppressing body weight gain, reducing body weight, or preventing, alleviating, or treating obesity of a mammal having CETP according to claim 2, wherein the effective component is administered at an effective dose for suppressing increase of (i) cholesteryl ester transfer protein (CETP) activity, (ii) low-density lipoprotein Cholesterol (LDL-C) level, or (iii) CETP activity and LDL-C level.

11. The method for suppressing body weight gain, reducing body weight, or preventing, alleviating, or treating obesity of a mammal having CETP according to claim 2, wherein the agent is free from DHA, a pharmaceutically acceptable salt thereof, an ester thereof, or a derivative thereof.

12. The method for suppressing body weight gain, reducing body weight, or preventing, alleviating, or treating obesity of a mammal having CETP according to claim 2, wherein the obesity is induced by intake of high fat diet.

13. The method for suppressing body weight gain, reducing body weight, or preventing, alleviating, or treating obesity of a mammal having CETP according to claim 2, comprising the step of administering a blended drug containing at least one member selected from EPA, a pharmaceutically acceptable salt thereof, an ester thereof, and a derivative thereof as its first effective component and at least one cholesteryl ester transfer protein (CETP) inhibitor as its second effective component.

14. The method for suppressing body weight gain, reducing body weight, or preventing, alleviating, or treating obesity of a mammal having CETP according to claim 2, wherein the cholesteryl ester transfer protein (CETP) inhibitor is dalcetrapib or anacetrapib.

15. The method for suppressing body weight gain, reducing body weight, or preventing, alleviating, or treating obesity of a mammal having CETP according to claim 1, wherein the patient is suffering from obesity of a type wherein enhancement of hepatic lipogenesis or fatty liver is not recognized.

16. The method for suppressing body weight gain, reducing body weight, or preventing, alleviating, or treating obesity of a mammal having CETP according to claim 6, wherein the obesity is induced by continuous intake of high fat diet.

17. The method for suppressing body weight gain, reducing body weight, or preventing, alleviating, or treating obesity of a mammal having CETP according to claim 12, wherein the obesity is induced by continuous intake of high fat diet.

18. A method for suppressing body weight gain, reducing body weight, or preventing, alleviating, or treating obesity of a mammal having cholesteryl ester transfer protein (CETP), comprising the step of administering a composition comprising:
- an agent for suppressing body weight gain or reducing body weight or an anti-obesity agent containing at least one member selected from EPA, a pharmaceutically acceptable salt thereof, an ester thereof, and a derivative thereof as its effective component,
- less than 2% by weight of at least one member selected from the group consisting of docosahexaenoic acid (DHA), a pharmaceutically acceptable salt thereof, an ester thereof, and a derivative thereof, and
- less than 2% by weight of a long chain unsaturated fatty acid of arachidonic acid;
- for combined administration with at least one compound selected from cholesteryl ester transfer protein (CETP) inhibitors which is a second effective component.

19. The method for suppressing body weight gain, reducing body weight, or preventing, alleviating, or treating obesity of a mammal having CETP according to claim 18, comprising the step of administering a blended drug containing at least one member selected from EPA, a pharmaceutically acceptable salt thereof, an ester thereof, and a derivative thereof as its first effective component and at least one CETP inhibitor as its second effective component.

20. The method for suppressing body weight gain, reducing body weight, or preventing, alleviating, or treating obesity of a mammal having CETP according to claim 18, wherein the CETP inhibitor is dalcetrapib or anacetrapib.

21. The method for suppressing body weight gain, reducing body weight, or preventing, alleviating, or treating obesity of a mammal having CETP according to claim 19, wherein the CETP inhibitor is dalcetrapib or anacetrapib.

* * * * *